(12) United States Patent
Seki et al.

(10) Patent No.: US 9,719,922 B2
(45) Date of Patent: Aug. 1, 2017

(54) OPTICAL SYSTEM AND OPTICAL QUALITY MEASURING APPARATUS

(71) Applicant: CANON KABUSHIKI KAISHA, Tokyo (JP)

(72) Inventors: Takashi Seki, Tokyo (JP); Hiroyuki Yuki, Utsunomiya (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/632,438

(22) Filed: Feb. 26, 2015

(65) Prior Publication Data

US 2015/0247798 A1    Sep. 3, 2015

(30) Foreign Application Priority Data

Feb. 28, 2014  (JP) ................. 2014-038061

(51) Int. Cl.
*G01N 21/57* (2006.01)
*G01B 11/30* (2006.01)

(52) U.S. Cl.
CPC .......... *G01N 21/57* (2013.01); *G01B 11/303* (2013.01); *G01N 2201/061* (2013.01)

(58) Field of Classification Search
CPC . G01N 21/57; G01N 2201/061; G01B 11/303
USPC .............. 356/237.1–237.5, 601–640
See application file for complete search history.

(56) References Cited

U.S. PATENT DOCUMENTS

| | | | |
|---|---|---|---|
| 3,997,268 A * | 12/1976 | Fladda | G01B 11/0616 356/429 |
| 3,999,864 A | 12/1976 | Mutter | |
| 4,218,144 A * | 8/1980 | Whitehouse | G01N 21/55 250/208.2 |
| 4,452,534 A | 6/1984 | Gribanov et al. | |
| 4,540,887 A | 9/1985 | Minerd et al. | |
| 4,914,309 A | 4/1990 | Masaharu et al. | |

(Continued)

FOREIGN PATENT DOCUMENTS

| | | |
|---|---|---|
| CN | 201819881 U | 5/2011 |
| GB | 1444780 A | 8/1976 |

(Continued)

OTHER PUBLICATIONS

Office Action issued in U.S Appl. No. 14/630,950 mailed Apr. 8, 2016.

(Continued)

*Primary Examiner* — Sang Nguyen
(74) *Attorney, Agent, or Firm* — Rossi, Kimms & McDowell LLP

(57) ABSTRACT

An optical system comprising: a light source; a photodetector; a first light-receiving system for causing the photodetector to receive first reflected light with a first angle of reflection from a surface; and a second light-receiving system for causing the photodetector to receive second reflected light with a second angle of reflection, different from the first angle of reflection, from the surface is provided. Here, a first light-receiving area of the photodetector with respect to light, of reflected light from the surface, via the first light-receiving system is spaced apart from a second light-receiving area of the photodetector with respect to light, of the reflected light from the surface, via the second light-receiving system.

20 Claims, 5 Drawing Sheets

(56) References Cited

U.S. PATENT DOCUMENTS

| | | | |
|---|---|---|---|
| 5,017,798 | A | 5/1991 | Murakami et al. |
| 6,122,042 | A | 9/2000 | Wunderman et al. |
| 6,215,552 | B1 | 4/2001 | Acquaviva et al. |
| 6,233,053 | B1 | 5/2001 | Preston et al. |
| 6,249,341 | B1 * | 6/2001 | Basiji .................. G01J 3/2803 356/318 |
| 6,292,576 | B1 | 9/2001 | Brownlee |
| 6,428,171 | B1 * | 8/2002 | Aoki .................. G01B 11/0608 250/559.38 |
| 6,509,964 | B2 | 1/2003 | Wiles et al. |
| 6,600,167 | B2 | 7/2003 | Sano |
| 6,770,863 | B2 * | 8/2004 | Walley ................. G01B 11/002 250/221 |
| 7,071,922 | B2 * | 7/2006 | Sun ..................... G06F 3/0312 345/157 |
| 7,391,518 | B1 | 6/2008 | Schwarz et al. |
| 7,675,020 | B2 | 3/2010 | Machida |
| 7,944,562 | B2 * | 5/2011 | Schwarz ............. G01N 21/8806 356/237.1 |
| 8,730,168 | B2 * | 5/2014 | Moyer ................. G06F 3/0317 345/163 |
| 2002/0171826 | A1 | 11/2002 | Wiles et al. |
| 2006/0109453 | A1 * | 5/2006 | Swift .................. G01B 11/306 356/139.03 |
| 2006/0227322 | A1 * | 10/2006 | Kauffman .............. G01J 3/02 356/328 |
| 2006/0243928 | A1 | 11/2006 | Blythe et al. |
| 2007/0024870 | A1 * | 2/2007 | Girard ................. G01B 11/002 356/623 |
| 2009/0073203 | A1 * | 3/2009 | Takekoshi ............. B41J 2/2114 347/9 |
| 2012/0167663 | A1 | 7/2012 | Groitzsch et al. |

FOREIGN PATENT DOCUMENTS

| | | |
|---|---|---|
| JP | 2001041888 A | 2/2001 |
| JP | 2001264251 A | 9/2001 |
| WO | 2004097383 A1 | 11/2004 |

OTHER PUBLICATIONS

European Search Report issued in European application No. EP15156855.7, dated Jun. 24, 2015. Cited in U.S. related U.S. Appl. No. 14/630,950.

European Search Report issued in European counterpart application No. EP15156856.5, dated Jul. 21, 2015.

* cited by examiner

OPTICAL SYSTEM AND OPTICAL QUALITY MEASURING APPARATUS

BACKGROUND OF THE INVENTION

Field of the Invention

The present invention relates to an optical system and an optical quality measuring apparatus.

Description of the Related Art

Feeling of gloss (feeling of glossiness, optical quality) of an object such as printed matters, coatings, and plastic materials is an important factor for quality of the object. There have been conventionally various indexes according to characteristics of a surface to be detected serving as a concrete value representing the feeling of gloss, and measuring methods for the indexes. For example, these indexes comprise specular glossiness, haze and image clarity, spectral characteristics and the like. Japanese Patent Laid-Open No. 2001-41888 discloses a method for estimating and determining feeling of gloss by combining indexes measured by a plurality of mutually differing light-receiving angles in order to reduce difference between the glossiness serving as a value representing the feeling of gloss and the feeling of gloss actually felt by sight.

However, the method disclosed by Japanese Patent Laid-Open No. 2001-41888 uses photodetectors different from each other depending on each of the plurality of light-receiving angles. Therefore, the method disclosed by Japanese Patent Laid-Open No. 2001-41888 increases the provided number of the photodetectors by increasing the variation of the light-receiving angles in order to improve precision (accuracy) of the glossiness, and causes the configuration of an optical system to become complicated. In contrast, a conventional optical system exists in which the configuration is simplified by using the common photodetector to a plurality of measurements with the plurality of light-receiving angles. However, in the optical system using the shared photodetector, light irradiated at the measurement with one light-receiving angle can enter an optical path used in the measurement with another light-receiving angle to output a signal with noise by the photodetector.

SUMMARY OF THE INVENTION

The present invention provides, for example, an optical system advantageous in terms of simplification of a configuration thereof and accuracy of measurement thereby.

According to an aspect of the present invention, an optical system comprising: a light source; a photodetector; a first light-receiving system for causing the photodetector to receive first reflected light with a first angle of reflection from a surface; and a second light-receiving system for causing the photodetector to receive second reflected light with a second angle of reflection, different from the first angle of reflection, from the surface is provided, wherein a first light-receiving area of the photodetector with respect to light, of reflected light from the surface, via the first light-receiving system is spaced apart from a second light-receiving area of the photodetector with respect to light, of reflected light from the surface, via the second light-receiving system.

Further features of the present invention will become apparent from the following description of exemplary embodiments (with reference to the attached drawings).

DESCRIPTION OF THE EMBODIMENTS

Hereinafter, preferred embodiments of the prevent invention are described with reference to the drawings.

(First Embodiment)

Figure 1A:
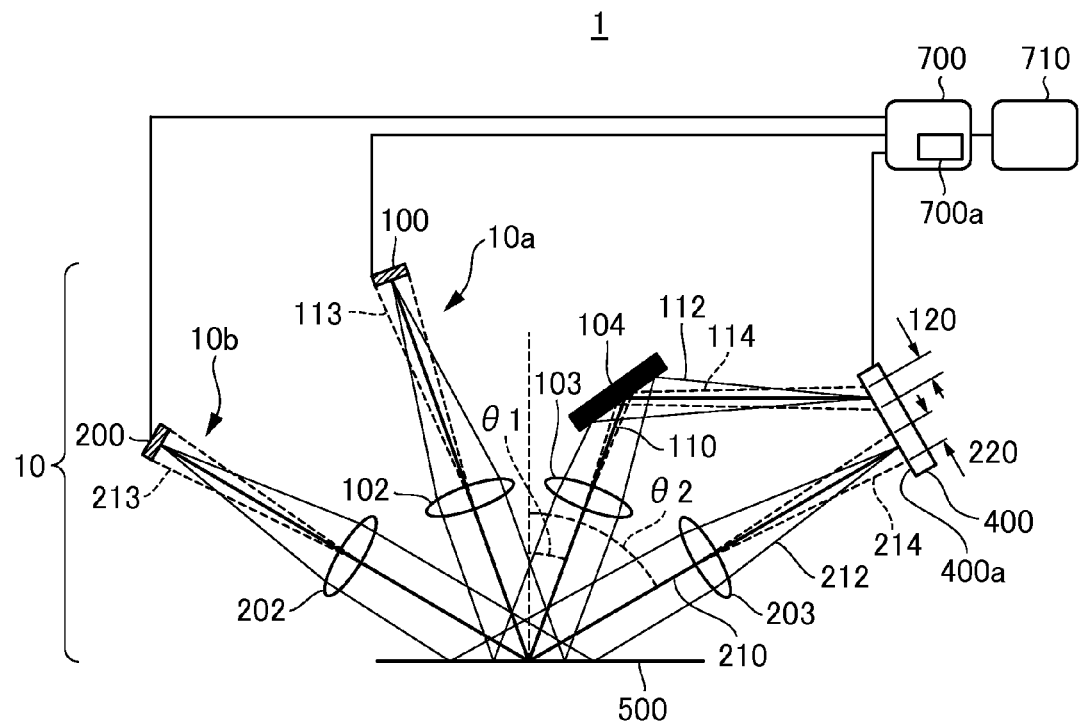
FIG. 1A illustrates a configuration of a glossmeter having an optical system according to a first embodiment of the present invention.
Figure 1B:
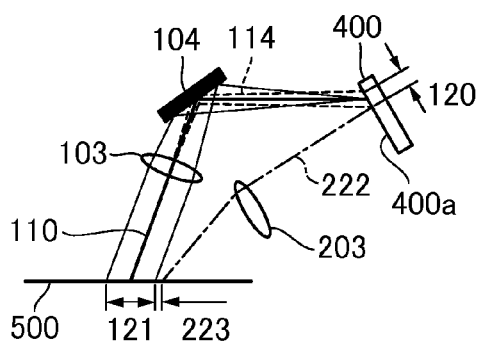
FIG. 1B illustrates a measurement state by a first optical system of the glossmeter as shown in FIG. 1A.
Figure 1C:
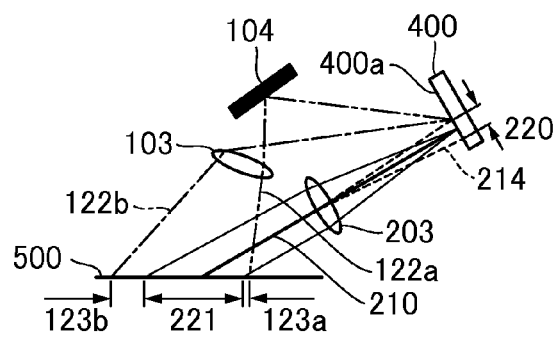
FIG. 1C illustrates a measurement state by a second optical system of the glossmeter as shown in FIG. 1A.

Firstly, a description will be given of an optical system according to a first embodiment of the present invention, and a glossmeter (an optical quality measuring apparatus) using the optical system. FIG. 1A to 1C are schematic diagrams of a glossmeter 1 that includes an optical system 10 according to the present embodiment. The glossmeter 1 measures glossiness of a surface of an object (also, referred to as a surface to be detected 500; a "subject surface" or a "surface") by using light. Hereinafter, the optical (visual) quality is referred to as "feeling of gloss (glossiness)", and an index representing the feeling of gloss such as specular glossiness, haze, or image clarity is referred to as "glossiness". For example, as an international standard, the specular glossiness is defined by the JIS-Z8741, and the haze is defined by the ASTM-E430, and the image clarity (DOI) is defined by the JIS-K7374 and the ASTM-D5767. Also, the international standard defines an aperture angle of a light source image (an aperture angle of a light-projecting system), an aperture angle of a photodetector (an aperture angle of a light-receiving system), an incident angle and a light-receiving angle as described in, for example, a fourth chapter "Measurement Conditions" in the JIS-Z8741. Therefore, in the present embodiment, sizes, configurations, and arrangements of a lens, a deflector, the photodetector and the like in the glossmeter 1 are set to satisfy a minimum basic condition described in the international standard. Note that this condition is not intended to limit the present invention, and the present invention may also be applied to the measurement of the glossiness with the originally defined aperture angle and the like. Thus, the glossmeter 1 adopts the optical system 10 with a plurality of light-receiving angles (angles of reflection) different from each other to more correctly comprehend the feeling of gloss. Here, the light-receiving angles have the same definition as that defined by the JIS-Z8741. Hereinafter, in the present embodiment, as an example, a description will be given of the optical system 10 comprising two optical systems in which two certain light-receiving angles are set to θ1 and θ2 (θ1<θ2).

FIG. 1A illustrates a configuration of the glossmeter 1. The glossmeter 1 comprises the optical system 10 and a control unit 700 (also, referred to as a "processing unit").

The optical system 10 includes a first optical system 10a and a second optical system 10b that set the respective receiving light angles so as to be different from each other. The first optical system 10a includes a first light source 100, a first light-projecting system 111, and a first light-receiving system 121. The second optical system 10b includes a second light source 200, a second light-projecting system 211, and a second light-receiving system 221. Here, the first light-receiving angle θ1 in the first optical system 10a (the first angle of reflection) is formed by the normal to the surface to be detected 500 and an optical axis 120 of the first light-receiving system 121. In contrast, the second light-receiving angle θ2 in the second optical system 10b (the second angle of reflection) is formed by the normal to the surface to be detected 500 and an optical axis 220 of the second light-receiving system 221. Furthermore, the optical system 10 includes a photodetector 400 able to receive the light from the two light-receiving systems of the first light-receiving system 121 and the second light-receiving system 221. In other words, the photodetectors that may be respectively included in the first optical system 10a and the second optical system 10b are shared as the single photodetector 400. In the present embodiment, each light-receiving angle θ1 and θ2 has various measuring items such as 20°, 45°, 60°, 75°, and 85° if the angles correspond to the international standard, and preferably, the angles are set depending on these measuring items and the like suitably.

Each light source 100 and 200 irradiates the light to each light-projecting side lens 102 and 202. Preferably, each light source 100 and 200 emits D65-type or C-type of standard light that is non-polarizing, and for example, white LED may be used, since it has less sequential drift and is inexpensive. Note that if the light source itself does not have the characteristics of the spectral distribution of the standard light such as the above examples, a colored glass filter may be arranged between the light source and the surface to be detected 500 to adjust the characteristics of the spectral distribution. Furthermore, while the first light source 100 and the second light source 200 are set as the light sources independent of each other in the present embodiment, the present invention is not limited thereto. For example, one illuminant (light source) is included in the optical system 10, and a beam splitter, a fiber coupler, or the like may be added to branch the light into a plurality of parts (two parts if these components corresponds to the present embodiment) to enable controlling the passing of the light by openable/closable openings.

The first light-projecting side lens 102 is a collecting lens as a first light-projecting system for allowing the light exiting from the first light source 100 to be incident to the surface to be detected 500 to generate first reflected light. Also, the second light-projecting side lens 202 is a collecting lens as a second light-projecting system for allowing the light exiting from the second light source 200 to be incident to the surface to be detected 500 to generate second reflected light. In the international standard, a positional relationship between the first light source 100 and the first light-projecting side lens 102 is defined by an aperture angle of a light-projecting system 113 and the optical magnification of the first optical system 10a. Also, the positional relationship between the second light source 200 and the second light-projecting side lens 202 is defined by an aperture angle of a light-projecting system 213 and the optional magnification of the second optical system 10b. The aperture angle of the light-projecting system 113 is an aperture angle of the first light source 100 seen from the first light-projecting side lens 102. Also, the aperture angle of the light-projecting system 213 is an aperture angle of the second light source 200 seen from the second light-projecting side lens 202. Here, a value for multiplying the optical magnification of the first optical system 10a by the aperture angle of the light-projecting system 113 and a value for multiplying the optical magnification of the second optical system 10b by the aperture angle of the light-projecting system 213 are set as defined values to apply the optical system 10 to the international standard. Note that although each light-projecting side lens 102 and 202 is illustrated as respective light-projecting systems, a plurality of lenses, deflectors, and the like may be combined for the additional improvement of the performance and the alteration of the arrangement. Also, each light-projecting side lens 102 and 202 may irradiate the collimate light, and may collect or emit luminous flux to the surface to be detected 500. Also, if the light source alone cannot deal with the adjustment of the light, a light-projecting side slit may be arranged to the first light source 100 or the second light source 200 as a secondary light source. Also, as shown in FIG. 1 of the JIS-Z8741, an intermediate image is provided and the intermediate imaging surface is set as a secondary light source surface. Thus, if the first light source 100 is arranged at the focal surface of the first light-projecting side lens 102, and in contrast, the second light source 200 is arranged at the focal surface of the second light-projecting side lens 202 to allow the collimate light to be incident to the surface to be detected 500, the arrangement conforms to the JIS-Z8741.

The first light-receiving side lens 103 is a collecting lens as a first light-receiving system for allowing regular reflected light (specular reflected light) in the first reflected light that is incident from the first light-projecting side lens 102 and then reflected on the surface to be detected 500 and the vicinity reflected light thereof to be incident to the photodetector 400. Also, the second light-receiving side lens 203 is a collecting lens as a second light-receiving system for allowing the regular reflected light in the second reflected light that is incident from the second light-projecting side lens 202 and then reflected on the surface to be detected 500 and the vicinity reflected light thereof to be incident to the photodetector 400. Here, the aperture angle of the light-receiving angle is also defined by the international standard as the aperture angle of the light-projecting system. An aperture angle of a light-receiving system 114 is an aperture angle of the photodetector 400 seen from the first light-receiving side lens 103, and is determined by the first light-receiving side lens 103 and a light-receiving side slit (not shown) arranged just in front of the photodetector 400. Also, an aperture angle of a light-receiving system 214 is an aperture angle of the photodetector 400 seen from the second light-receiving side lens 203, and is determined by the second light-receiving side lens 203 and the light-receiving side slit (not shown) arranged just in front of the photodetector 400. Note that a deflector, such as a prism, an eccentric lens, or a diffraction grating may be set as instead of the reflector 104, while the reflector 104 may be, for example, a mirror. Furthermore, the reflector 104 may be a plurality of reflectors and may be included in both of the first optical system 10a and the second optical system 10b. Also, although each light-receiving side lens 103 and 203 is illustrated as respective light-receiving systems, the systems may include the plurality of lenses, the deflectors and the like for the additional improvement of the performance and the alteration of the arrangement and the like. Furthermore, the reflector 104 may be a doublet lens instead of the collecting lens as each light-projecting side lens and each light-receiving side lens, from the viewpoint of the improved aberration.

The photodetector 400 is arranged such that the position of a light-receiving surface 400a of the photodetector 400 align with a focusing point of the reflector 104 and the first light-receiving side lens 103 or is within the Rayleigh length thereof, and aligns with the focusing point of the second light-receiving side lens 203 or is within the Rayleigh length thereof. The photodetector 400 may adopt an imaging element (solid imaging element) such as, for example, a CCD or a CMOS. The use of such an imaging element has the advantage of being capable of picking up and processing the information about amount of the light of pixels corresponding to a slit in the following controller 700 without providing the opening shown in FIG. 1 of the JIS-Z8741 (light-receiving side slit S2). Also, the angle distribution of the reflected light can be acquired to calculate the haze defined in the ASTM-E430 or the image clarity defined in the ASTM-D5767 by the controller 700. In addition, if the imaging element is a colored type, the controller 700 can also acquire a signal depending on the hue to acquire spectrum information. Note that the photodetector 400 may be combined with the light-receiving side slit S2 as shown in the above JIS-Z8741. In this case, the light-receiving side slit S2 is arranged near each light-receiving side lens 103 and 203.

Here, in the present embodiment, the first optical system 10a has a measured area (area to be measured) on the surface to be detected 500 identical to that of the second optical system 10b, and the optical axis 110 of the first light-receiving system is set so as to be approximately the same position as the optical axis 210 of the second light-receiving system on the surface to be detected 500. Due to the above same position of the area and the optical axis, the glossiness of each light-receiving angle θ1 and θ2 is not affected by the in-plane error of the quality in the surface to be detected 500. Also, the first optical system 10a and the second optical system 10b are regular reflection optical systems that set the surface to be detected 500 so as to be a specular surface and the projecting light angle is equal to the light-receiving angle with respect to the surface to be detected 500.

Also, in the present embodiment, the positional relationship between the surface to be detected 500, the first light-receiving side lens 103, the reflector 104, and the second light-receiving side lens 203 satisfies the following two conditions. Firstly, a first condition is a condition that when the glossiness is measured by using the first optical system 10a, in the light-receiving surface 400a, a first light-receiving area 120 for receiving the first reflected light is spaced apart from a light-receiving area via a second detour for receiving the light arriving via another second optical system 10b in the first reflected light. Also, a second condition is a condition that when the glossiness is measured by using the second optical system 10b, in the light-receiving surface 400a, a second light-receiving area 220 for receiving the second reflected light is spaced apart from a light-receiving area via a first detour for receiving the light arriving via another first optical system 10a in the second reflected light. In the present embodiment, the "light-receiving area" is an area with the aperture angle of the light-receiving system on the light-receiving surface 400a.

The controller 700 is connected to each light source 100 and 200 and the photodetector 400 via electric wires. Additionally, the controller 700 allows either of the first light source 100 or the second light source 200 to emit the light in accordance with the measurement to acquire the glossiness based on the information (output) from the photodetector 400 (acquire the information about the glossiness). In this processing, the controller 700 controls the timing of the emitting of the light from the first light source 100 and the second light source 200, and the amount of the light, the irradiation time, and the like at each timing of the emitting of the light. Also, the controller 700 comprises a storage device 700a, and is connected to a display device 710 via the electric wires. The display device 710 is, for example, a liquid crystal display, and may display the glossiness derived from the controller 700.

Figure 6A:
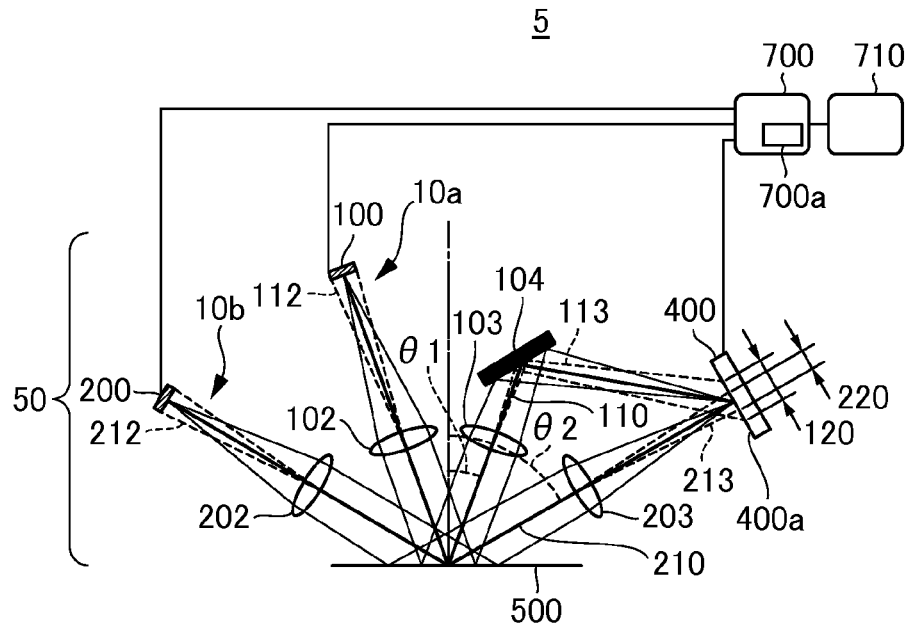
FIG. 6A illustrates a configuration of a glossmeter having a conventional optical system.
Figure 6B:
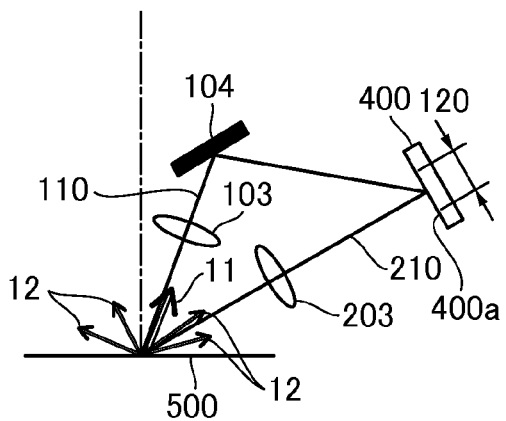
FIG. 6B illustrates a measurement state by a first optical system of the glossmeter as shown in FIG. 6A.
Figure 6C:
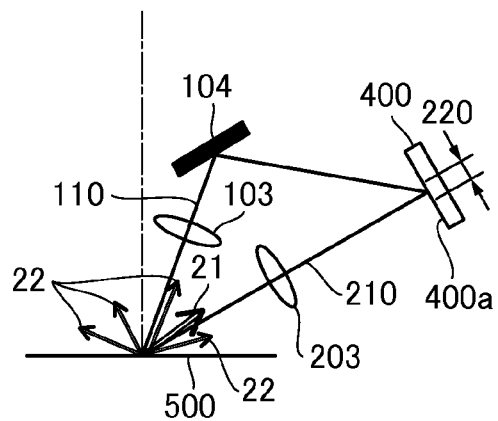
FIG. 6C illustrates a measurement state by a second optical system of the glossmeter as shown in FIG. 6A.

Next, a description will be given of a glossmeter with a conventional optical system as a comparison example to define the characteristics of the present embodiment. FIG. 6A to FIG. 6C are schematic diagrams illustrating a configuration of a glossmeter 5 that includes a conventional optical system 50. Note that in the optical system 50, components corresponding to those of the optical system 10 have the same reference numbers as those of the optical system 10 to simplify the comparison to the glossmeter 1 with the optical system 10 according to the present embodiment, and also a surface to be detected 500 and a controller 700 in the optical system 50 have same numbers as those in the glossmeter 1. Furthermore, the glossmeter 5 calculates the glossiness with two light-receiving angles θ1 and θ2 that different from each other, and the use of the photodetector 400 common to the both measurements are similar to those of the glossmeter 1 in the present embodiment.

FIG. 6A illustrates a configuration of the glossmeter 5. As shown in FIG. 6A, the first light receiving area 120 is overlapped with the second light-receiving area 220 in the first optical system 10a and the second optical system 10b included in the optical system 50. FIG. 6B is a schematic diagram illustrating a state in which each light-receiving side lens 103 and 203 and the photodetector 400 are extracted from FIG. 6A, and the measurement is performed by the first optical system 10a. In this case, when the first light source 100 irradiates light to the surface to be detected 500, regular reflected light 11 and diffuse reflected light 12 are generated on the surface to be detected 500. The regular reflected light 11 and the vicinity reflected light thereof are irradiated to the photodetector 400 via the first light-receiving side lens 103. However, a portion of the diffuse reflected light 12 enters to an optical path of the second optical system 10b that is an optical system different from the first optical system 10a, and is irradiated to the photodetector 400 via (by detouring) the second light-receiving side lens 203. Accordingly, in this state, the regular reflected light 11 in the first optical system 10a that should be obtained, and the diffuse reflected light 12 in the second optical system 10b that is unnecessary overlap each other on the first light-receiving area 120. Since the glossiness is calculated based on the received light information of the regular reflected light 11 and the vicinity reflected light thereof, the diffuse reflected light 12 received via the second light-receiving side lens 203 becomes noise, and can affect the calculated value.

In contrast, FIG. 6C is a schematic diagram illustrating a state in which each light-receiving side lens 103 and 203 and the photodetector 400 are extracted from FIG. 6A, and the measurement is performed by the second optical system 10b. In this case, when the second light source 200 irradiates light to the surface to be detected 500, regular reflected light 21 and diffuse reflected light 22 are generated on the detected surface 500. The regular reflected light 21 and the vicinity reflected light thereof are irradiated to the photodetector 400 via the second light-receiving side lens 203. However, a portion of the diffuse reflected light 22 enters the optical path of the first optical system 10a that is different from the second optical system 10b, and is irradiated to the photodetector 400 via (by detouring) the first light-receiving side lens 103. Accordingly, in this state, the regular reflected light 21 in the second optical system 10b that should be obtained and the diffuse reflected light 22 in the second optical system 10b that is unnecessary overlap each other on the second light-receiving area 220. Thus, as described above, the diffuse reflected light 22 received via the first light-receiving side lens 103 becomes noise, and can affect the calculated value. Additionally, in the present embodiment, the first light-receiving area 120 of the photodetector 400 for the light via the first light-receiving system in the reflected light on the surface to be detected 500 is set to be spaced apart from the second light-receiving area 220 of the photodetector 400 for the light via the second light-receiving system.

FIG. 1B is a schematic diagram illustrating a state in which the first light-receiving side lens 103, the reflector 104, the second light-receiving side lens 203 and the photodetector 400 are extracted from FIG. 1A and the measurement is performed by the first optical system 10a. Firstly, in the first optical system 10a of FIG. 1B, a first measuring area 121 on the surface to be detected 500 (surface) is a set of the positions where the light arrives if the light is directed from any point of the first light-receiving area 120 to the surface to be detected 500 via the reflector 104 and the first light-receiving side lens 103. In contrast, a second non-measuring area 223 on the surface to be detected 500 is an area that is unnecessary for the substantial measurement, and a set of the positions where the light arrives if the light is directed from any point of the first light-receiving area 120 to the surface to be detected 500 via the second light-receiving side lens 203. In other words, the second non-measuring area 223 is the area where the diffuse reflected light generated on the detected surface 500 may be incident to the first light-receiving area 120 via the second light-receiving side lens 203. Note that unnecessary light 222 shown in FIG. 1B refers to the outermost periphery light of the second non-measuring area 223. In other words, if the first measuring area 121 is spaced apart from the second non-measuring area 223 as shown in FIG. 1A, the diffuse reflected light generated in the first measuring area 121 is never incident to the first light-receiving area 120 at the measurement using the first optical system 10a.

In contrast, FIG. 1C is a schematic diagram illustrating a state in which the first light-receiving side lens 103, the reflector 104, the second light-receiving side lens 203, and the photodetector 400 are extracted from FIG. 1A, and the measurement is performed by the second optical system 10b with the second light-receiving angle θ2. Firstly, in the second optical system 10b of FIG. 1C, a second measuring area 221 on the surface to be detected 500 is a set of the positions where the light arrives if the light is directed from any point of the second light-receiving area 220 to the surface to be detected 500 via the second light-receiving side lens 203. In contrast, a first non-measuring area 123 on the surface to be detected 500 is a set of the positions where the light arrives if the light is directed from any point of the second light-receiving area 220 to the surface to be detected 500. In other words, the first non-measuring area 123 is an area in which the diffuse reflected light generated on the surface to be detected 500 may be incident to the second light-receiving area 220 via the first light-receiving side lens 103 and the reflector 104. Note that a "1A" non-measuring area 123a is a set of the positions where the light arrives via the reflector 104 and the first light-receiving side lens 103, and unnecessary light 122a shown in FIG. 1C refers to the outermost periphery light of the "1A" non-measuring area 123a. In contrast, a "1B" non-measuring area 123b is a set of positions where the light arrives directly via the first light-receiving side lens 103 and not via the reflector 104, and unnecessary light 122b shown in FIG. 1C refers to the outermost periphery light of the "1B" non-measuring area 123b. In other words, if the second measuring area 221 is spaced apart from the first non-measuring area 123 as shown in FIG. 1A, the diffuse reflected light generated in the second measuring area 221 is never incident to the second light-receiving area 220 at the measurement using the second optical system 10b.

Figure 2:
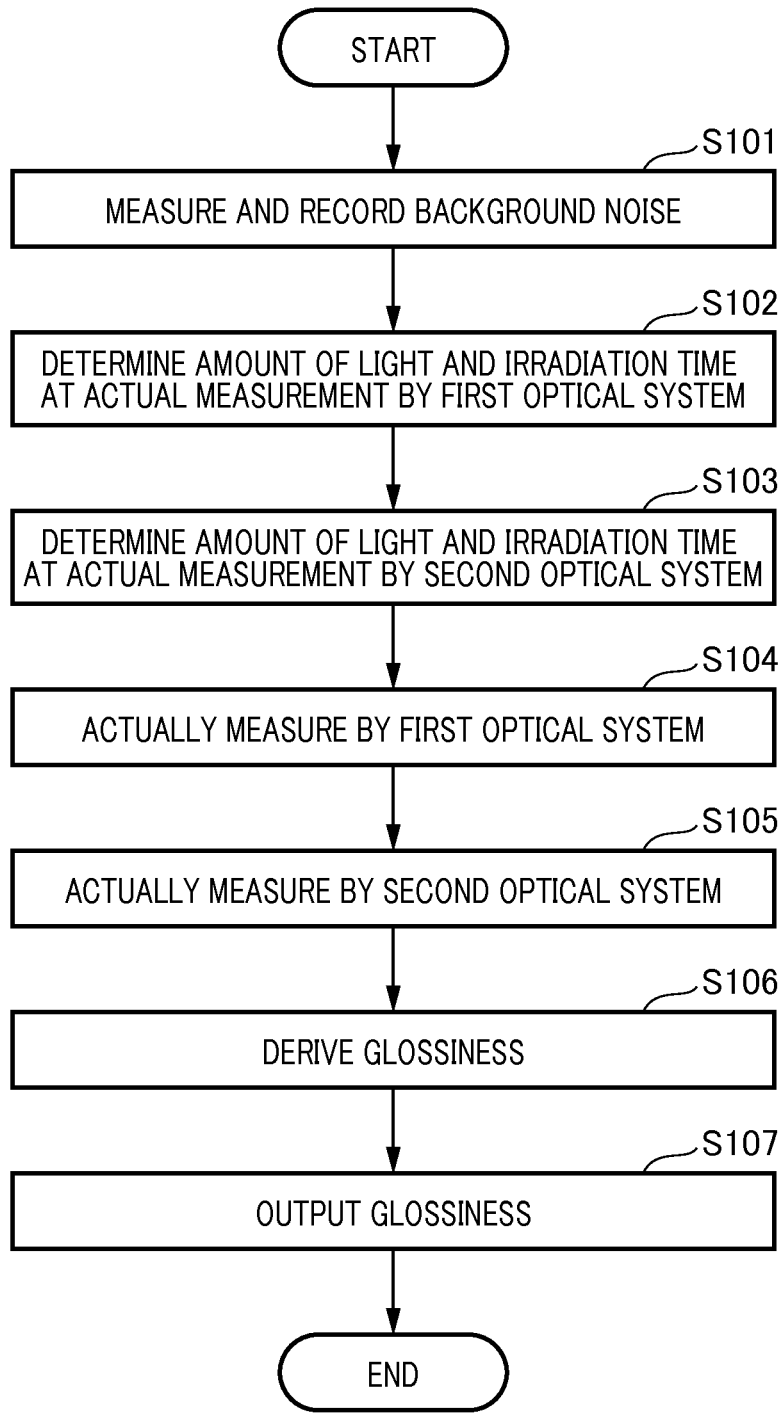
FIG. 2 is a flowchart illustrating a flow of measurement of the glossiness in the first embodiment.

Next, a description will be given of measurement for the glossiness by the glossmeter 1 with the optical system 10. FIG. 2 is a flow chart illustrating a flow of the measurement of the glossiness by the glossmeter 1. Firstly, the controller 700 measures a background noise of the photodetector 400 and records information about the background noise to the storage device 700a (step S101). In this step, the controller 700 sets states of the first light source 100 and the second light source 200 to "OFF", and in these states, monitors amount of the light received by the photodetector 400. Information about this amount of the light (first information about the amount of the light) is recorded in the storage device 700a. Note that if the background noise is determined to be sufficiently small, this step S101 may be omitted.

Next, the controller 700 preliminarily measures the glossiness by using the first optical system 10a, and determines the amount of the light and the irradiation time suitable for actual measurement (step S102). In this step, the state of the first light source 100 is set to "ON" and that of the second light source 200 is set to "OFF". Here, the controller 700 firstly confirms saturation of the photodetector 400 while allowing the first light source 100 to emit the light at a fixed time, and decreases the amount of the light to the light-emitting amount that does not produce the saturation. Next, the controller 700 determines the suitable amount of the light based on the amount of the light of the first light source 100, the amount of the light received by the photodetector 400, and the dynamic range of the photodetector 400. Also, the controller 700 determines the suitable irradiation time by referring to the information about the amount of the light based on the noise obtained in step S101 and the minimum amount of the light of the photodetector 400.

Next, the controller 700 preliminarily measures the glossiness by using the second optical system 10b and determines the amount of the light and the irradiation time suitable for the actual measurement as step S102 in the first optical system 10a (step S103). In this step, the state of the second light source 200 is set to "ON", and the state of the first light source 100 is set to "OFF". Note that the determination of the amount of the light and the irradiation time in the second optical system 10b is not always limited to the values by the preliminary measurement, and for example, to shorten the time of the determination, approximate values may be determined by referring to the amount of the light and the irradiation time in the first optical system 10a determined in step S102.

Next, the controller 700 actually measures the glossiness by using the first optical system 10a, and the amount of the light and the irradiation time determined in step S102 (step S104). In this step, the state of the first light source 100 is set to "ON", and the state of the second light source 200 is set be "OFF". Here, the controller 700 records information about the amount of the light received by the photodetector 400 (second information about the amount of the light) to the storage device 700a. Note that the controller 700 may obtain only the information about the amount of the light in a portion corresponding to a pixel of the first light-receiving area 120 from the photodetector 400 or obtain the information by excluding the pixel, in order to shorten the measuring time.

Next, the controller 700 actually measures the glossiness by using the second optical system 10b, and the amount of the light and the irradiation time determined in step S103 (step S105). In this step, the state of the second light source 200 is set to "ON", and the state of the first light source 100 is set be "OFF". Here, the controller 700 records information about the amount of the light received by the photodetector 400 (third information about the amount of the light) to the storage device 700a. In this step, the controller 700 may also obtain only the information about the amount of the light in a portion corresponding to a pixel of the second light-receiving system 220 from the photodetector 400 or obtain the information by excluding the pixel, in order to shorten the measuring time.

Next, the controller 700 derives the glossiness based on the first to third information about the amount of the light obtained in each step as described above (step S106). More specifically, first glossiness by the first optical system 10a can be obtained by subtracting the first information about the amount of the light 1 from the second information about the amount of the light, and performing arithmetic processing defined by, for example, the JIS-Z8741. Also, second glossiness by the second optical system 10b can be obtained by subtracting the first information about the amount of the light 1 from the third information about the amount of the light and performing the arithmetic processing. Note that the arithmetic processing adopted in the calculation of the glossiness may comprise a method defined by the above international standard and a method other than that defined by the international standard. The method other than that defined by the international standard comprises, for example, a method for acquiring a variable angle reflection distribution characteristic (spatial distributed characteristic of reflection) of the surface to be detected 500 by a measurement, and calculating the full width at one-half maximum value of this variable angle reflection distribution characteristic as the intensity of the vicinity light of the regular reflected light together with the intensity of the regular reflected light to calculate the glossiness based on these factors. Also, the method may comprise a method for irradiating the light to the surface to be detected 500 with an incident angle and acquiring an angle distribution function of the intensity of the scattered light by a measurement to calculate the glossiness based on the derivative value concerning the scattered angle of this function of the angle distribution.

Then the controller 700 outputs the glossiness obtained in step S106 (step S107). At this step, the controller 700, for example, transmits the glossiness information to the display device 710 to display this image. As another step, the controller 700, for example, may transmit the glossiness information to the outside via signal lines or continue to record the information to the storage device 700a.

Note that the flows in each step described above is not intended to limit the present invention, and the order of the steps may be changed. For, example, the step for measuring and recording the background noise in the step S101 may be performed at any time within the range performed before the step for calculating the glossiness in the step S106. Also, a portion of the step for calculating the glossiness in the step S106 may be performed at the same time as other steps.

Here, depending on each condition of optical distance between the surface to be detected 500 and the light-receiving system, an irradiation area in which the light exit from the light-projecting system is irradiated to the surface to be detected 500, or an effective pupil diameter of the light-receiving system, the reflected light close to the regular reflected light defined by the aperture angle of the light-receiving system (hereinafter, referred to as "vicinity reflected light") cannot be captured. When the glossiness is derived, it is desired that the vicinity reflected light is captured. Thus below, a description will be given of the condition in which the vicinity reflected light can be captured suitably.

Figure 3:
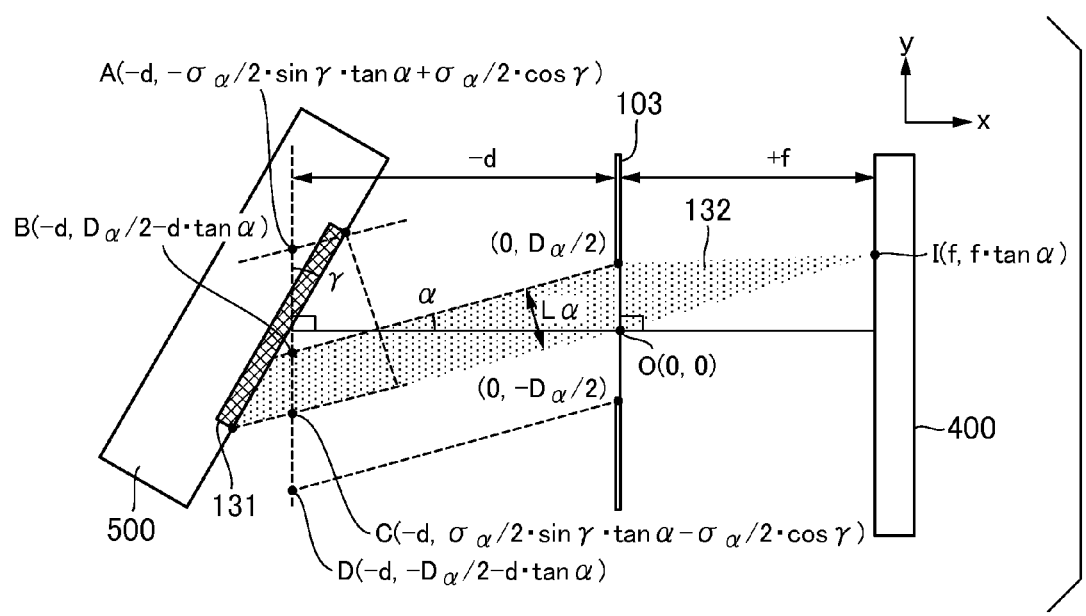
FIG. 3 illustrates a description of a condition for capturing vicinity reflected light.

FIG. 3 is a schematic diagram of a condition for capturing the vicinity reflected light and illustrates an optical arrangement from the surface to be detected 500 to the photodetector 400 in the first optical system 10a setting an incident surface as a cutting surface (a surface formed by a direction with an angle α in the international standard). The irradiation area 131 is an area in which the light exiting from the first light source 100 is irradiated to the surface to be detected 500 via the first light-projecting side lens 102. Luminous flux of reflected light 132 is light reflected in the direction of the angle α in the irradiation area 131 and is collected to the photodetector 400 via the first light-receiving side lens 103. Note that when the angle α is equal to 0°, the reflection is specular reflection. Here, the optical axis at the regular reflection is set as the x axis, and a straight line perpendicular to the x axis and passing a principal point of the first light-receiving side lens 103 in the incident surface is set as the y axis. Also, a diameter of an incident luminous flux in the incident surface to the surface to be detected 500 is set as σ, the effective pupil diameter in the incident surface of the first light-receiving side lens 103 is set as D. In addition, if the length of the irradiation area 131 in the y axis direction is set as $\sigma_\alpha$, the effective pupil diameter of the first light-receiving side lens 103 in the y axis direction is set as $D_\alpha$, the distance between the intersection of the x axis and the irradiation area 131 and the origin O is set as d, and the light-receiving angle is set as γ, the magnitude Lα of the Luminous flux of reflected light 132 is defined as following:

[Formula 1]

$$L\alpha = \begin{cases} l\alpha \cdot \cos\alpha & l\alpha > 0 \\ 0 & l\alpha \leq 0 \end{cases} \quad (1)$$

Note that lα is represent by a formula (2):
[Formula 2]

$$l\alpha = \min\{D_\alpha/2 - d\cdot\tan\alpha, -\sigma_\alpha/2\cdot\sin\gamma\cdot\tan\alpha + \sigma_\alpha/2\cdot\cos\gamma\} - \max\{-D_\alpha/2 - d\cdot\tan\alpha, \sigma_\alpha/2\cdot\sin\gamma\cdot\tan\alpha - \sigma_\alpha/2\cos\gamma\}. \quad (2)$$

Based on formula (1), if the light reflected in the direction of the angle α is received the photodetector 400, each value of $\sigma_\alpha$, $D_\alpha$, d, and γ may satisfy "Lα>0". The international standard defines the aperture angle of the light-receiving system with respect to the light-receiving angle γ. If this defined aperture angle of the light-receiving system is set as $\alpha_2$, the condition may be satisfied as the following formula (3) obtained by deforming the formula (1) to capture the vicinity reflected light within the aperture angle of the light-receiving system $\alpha_2$.

[Formula 3]

$$D_\alpha/2 - d \cdot \tan(\alpha_2/2) - \sigma_\alpha/2 \cdot \sin\gamma \cdot \tan(\alpha_2/2) + \sigma_\alpha/2 \cdot \cos\gamma > 0 \quad (3)$$

If the condition is adapted to the conditions defined by the ISO standard 2813, the ISO standard 7668, the JIS-Z8741, and the ASTM-D523, the aperture angle of the light-receiving system $\alpha_2$ is equal to 1.80, when the light-receiving angle $\gamma$ is equal to 20°. Accordingly, if a condition represented as the following formula (4) is satisfied, the optical system 10 can capture the light reflected in the direction of the angle $\alpha$.

[Formula 4]

$$D_\alpha/2 - 0.0157 \cdot d + 0.467 \cdot \sigma_\alpha > 0 \quad (4)$$

Also, since the aperture angle of the light-receiving system $\alpha_2$ is equal to 4.4, 4.4, 11.5, and 4.0 when the light-receiving angle $\gamma$ is equal to 45°, 60°, 75°, and 85° respectively, the optical system 10 can capture the light reflected in the direction of the angle $\alpha$ if the conditions of the following formulae are each satisfied.

[Formula 5]

$$D_\alpha/2 - 0.0384 \cdot d + 0.340 \cdot \sigma_\alpha > 0 \quad (5)$$

[Formula 6]

$$D_\alpha/2 - 0.0384 \cdot d + 0.233 \cdot \sigma_\alpha > 0 \quad (6)$$

[Formula 7]

$$D_\alpha/2 - 0.101 \cdot d + 0.081 \cdot \sigma_\alpha > 0 \quad (7)$$

[Formula 8]

$$D_\alpha/2 - 0.0035 \cdot d + 0.026 \cdot \sigma_\alpha > 0 \quad (8)$$

Also, to measure the haze of 20° defined by the ASTM-E430, the aperture angle of the light-receiving system $\alpha_2$ may be set equal to 2.8 at the 20° of the light-receiving angle $\theta$. Thereby, the optical system 10 can correctly measure the haze of 20° if the condition of the following formula (9) is satisfied.

[Formula 9]

$$D/2 - 0.0489 \cdot d + 0.461 \cdot \sigma_\alpha > 0 \quad (9)$$

As described above, the optical system 10 uses the same photodetector 400 for the plurality of light-receiving angles $\theta 1$ and $\theta 2$, which are different from each other, to enable reducing the provided number of the photodetectors compared to the conventional technique using the dedicated photodetectors adapted to each of the plurality of light-receiving angles, that is, the configuration is simplified. Also, the optical system 10 is arranged as described above to enable reducing the noise that may be included in the information (output) of the photodetector 400, while responding to measurements with the plurality of light-receiving angles to improve the precision for the acquisition of the information.

As described above, the present embodiment can provide an optical system advantageous in terms of simplification of a configuration thereof and accuracy of measurement thereby. Also, the glossmeter using this optical system is advantageous for the simplicity of the configurations of the glossmeter itself. In addition, the glossmeter calculates the glossiness based on the information with reduced noise from the photodetector 400 (optical system 10) to improve the accuracy of the comprehension of the feeling of gloss by the measurement.

(Second Embodiment)

Figure 4:
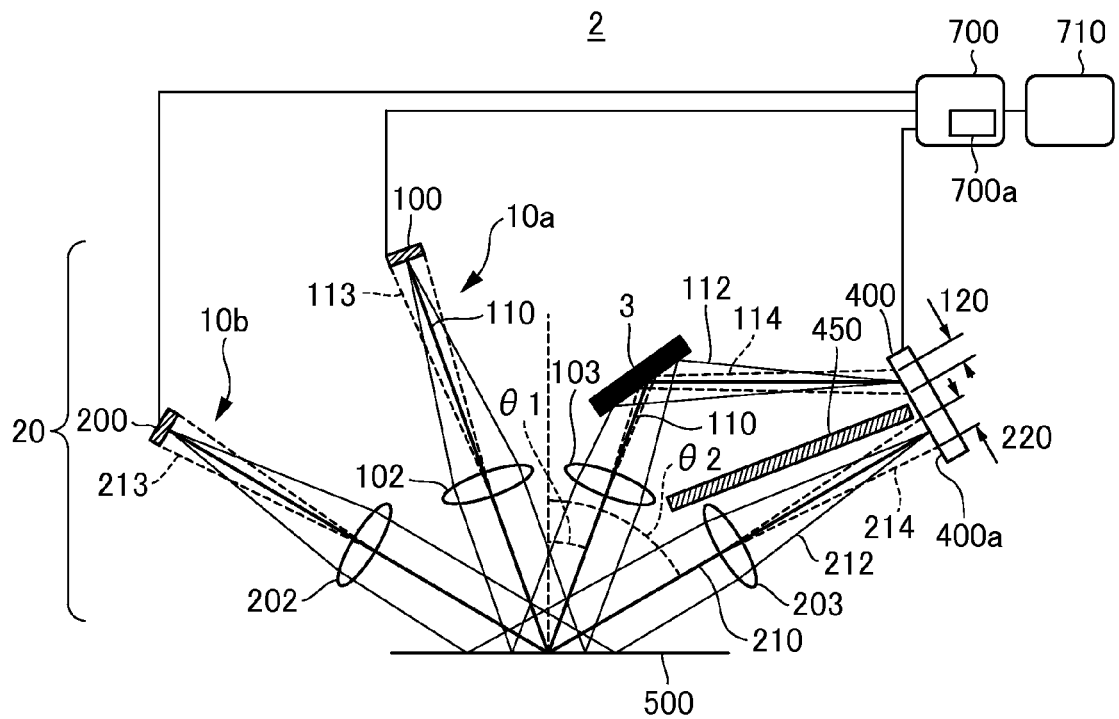
FIG. 4 illustrates a configuration of a glossmeter having an optical system according to a second embodiment of the present invention.

Next, a description will be given of an optical system according to a second embodiment of the present invention, and a glossmeter using the optical system. FIG. 4 is a schematic diagram illustrating a configuration of a glossmeter 2 that includes an optical system 20 according to the present embodiment. In the first embodiment, the glossmeter 1 with the optical system 10 suitably setting the arrangement of each light-receiving side lens 103 and 203, the reflector 104, and the like is described. In contrast, the characteristic of the optical system 20 and the glossmeter 2 according to the present embodiment is that these components comprise a shield close to the surface of the light-receiving surface 400a of the photodetector 400 in addition to the configuration of the optical system 10 according to the first embodiment. Note that in the glossmeter 2 according to the present embodiment, components that are the same as those of the glossmeter 1 in the first embodiment have the same reference number as those of the glossmeter 1, and then a detailed description thereof will be omitted.

A shield 450 is arranged at a position in which the shield 450 does not affect each light-receiving area 120 and 220, and the second light-receiving side lens 203 is not seen from any point of the first light-receiving area 120, and the first light-receiving side lens 103 is not seen from any point of the second light-receiving area 220. Also, the shield 450 is, for example, a plate with light shielding property. It is desired that the surface of the shield 450 is plated with black color to reduce the reflectance, or the surface processing such as the surface emboss processing is applied to the surface of the shield 450 to diffuse the light, in order to bring the reflectance close to zero regardless of the incident angle thereto. Also, the shield 450 may comprise a structure with directional characteristic of the reflection such as blazed shape to reduce ghost. Thereby, even if reflected light is intended to be incident from the light-receiving side lens not used in the measurement to the light-receiving area used in the measurement, the shield 450 suitably shades the reflected light.

Accordingly, the present embodiment provides improved certainty of the effect similar to that in the first embodiment. Note that the condition of the provided position of the shield 450 described above may not be satisfied in the present embodiment. For example, even if a portion of the second light-receiving side lens 203 is seen from any point of the first light-receiving area 120, or a portion of the first light-receiving side lens 103 is seen from any point of the second light-receiving system 220, a certain level of effect can be obtained as long as the condition of the first embodiment is satisfied. Also, the shield 450 is not limited to the plate as shown in FIG. 4, and it may be, for example, an aperture (a member with an opening), a lens barrel, or the like if the direction of the reflected light can be suitably defined.

(Third Embodiment)

Figure 5:
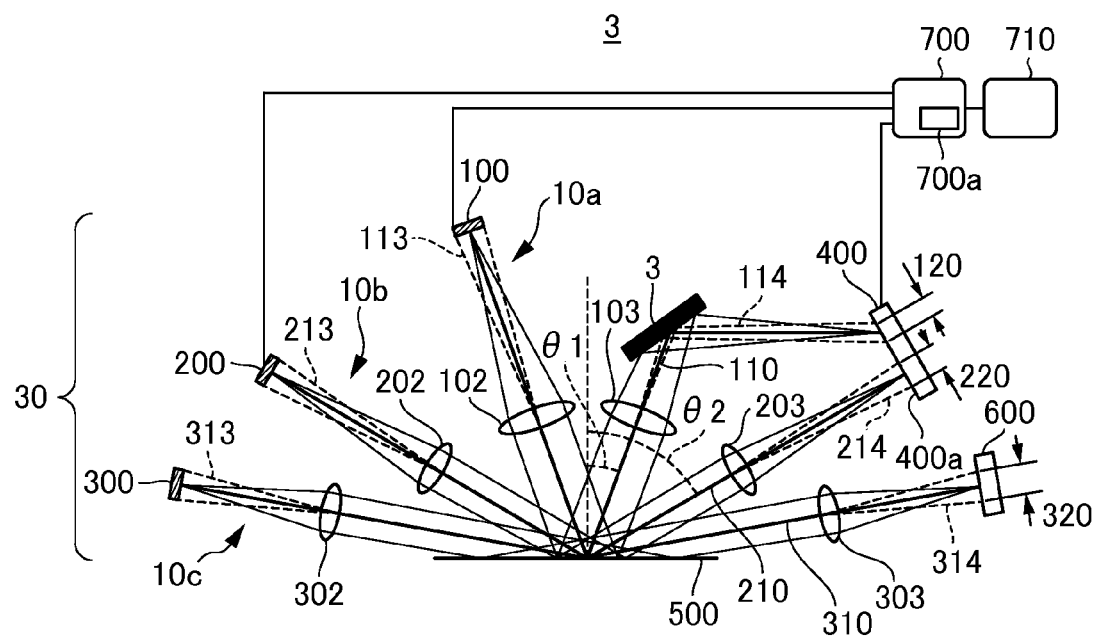
FIG. 5 illustrates a configuration of a glossmeter having an optical system according to a third embodiment of the present invention.

Next, a description will be given of an optical system according to a third embodiment of the present invention, and a glossmeter using the optical system. FIG. 5 is a schematic diagram illustrating a configuration of a glossmeter 3 that includes an optical system 30 according to the present embodiment. In the first embodiment, the glossmeter 1 with the optical system 10 for performing measurement with the light-receiving angles $\theta 1$ and $\theta 2$ which different from each other, and the single photodetector 400 is described. In contrast, the characteristics of the optical system 30 and the glossmeter 3 according to the present embodiment is that the components includes a third optical system 10c with a third light-receiving angle (third angle of reflection) $\theta 3$ that is different from the first light-receiving angle $\theta 1$ and the second light-receiving angle $\theta 2$, in addition to each optical system 10a and 10b in the first embodiment.

Note that components of the glossmeter 3 in the present embodiment that are the same as those of the glossmeter 1 have the same reference number as those of the glossmeter 1 in the first embodiment, and then, the detailed description thereof will be omitted.

The third optical system 10c includes a third light source 300, a third light-projecting side lens 302 as a third light-projecting system, a third light-receiving side lens 303 as a third light-receiving system, and a photodetector 600 that is different from the above photodetector 400. The third light source 300 irradiates the light to the third light-projecting side lens 302. The third light-projecting side lens 302 allows the light that exits from the third light source 300 to be collimated and incident to the surface to be detected 500, in order to generate third reflected light. The third light-receiving side lens 303 allows the regular reflected light in the reflected light reflected on the surface to be detected 500 and the vicinity reflected light thereof to be incident to the second photodetector 600. There is the regular reflected arrangement between the third light-projecting side lens 302 and the third light-receiving side lens 303. In the present embodiment, a start point of an optical axis 310 on the surface to be detected 500 in the third optical system 10c is approximately the same as a start point of the optical axis 210 on the surface to be detected 500 in the second optical system 10b as an example. Each light-receiving angle has a relationship of "$\theta1<\theta2<\theta3$". Note that the light-projecting system or the light-receiving system may form a bent optical path by using the deflector for a compact configuration. Additionally, an aperture angle of a light-projecting system 313, an aperture angle of a light-receiving system 314, and a third light-receiving area 320 are set in the third optical system 10c as in each optical system 10a and 10b described in the first embodiment. Note that the third light source 300 and the second photodetector 600 themselves may be types similar to each light source 100 and 200 and the photodetector 400 as described in the first embodiment.

Here, in the optical system 30 according to the present embodiment, if the three light-receiving angles $\theta1$ to $\theta3$ are set as, for example, 20°, 60°, and 85° respectively in the optical system 30 according to the present embodiment, the angles conform to the ISO standard 2813, the ASTM-D523, and the JIS-Z8741. Alternatively, if the three light-receiving angles $\theta1$ to $\theta3$ are set as 20°, 45°, and 60° respectively, the angles conform to the ISO standard 7668, the ASTM-D2457, and the JIS-Z8741. Also, if any of the three light-receiving angles $\theta1$ to $\theta3$ is set as 75°, the angles conform to the JIS-Z8741 of the measurement standard of the glossiness, especially for the use of papers. Furthermore, to correctly comprehend the feeling of gloss, for example, if the third light-receiving angle $\theta3$ is set in a direction different from the first light-receiving angle $\theta1$ and the second light-receiving angle $\theta2$ in the surface to be detected 500, the gloss anisotropy of the surface to be detected 500 can be measured.

As described above, the present embodiment can comprehend the feeling of gloss in more detail and measure other indices for glossiness, together with exhibiting the effect similar to the first embodiment. Note that although the optical system 30 according to the present embodiment comprises the three optical systems, the system may further add an optical system as the third optical system 10c, or may use a plurality of sets made by the two optical systems constituting the optical system 10 of the first embodiment.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-038061 filed Feb. 28, 2014, which is hereby incorporated by reference herein in its entirety.

What is claimed is:

1. An optical system comprising:
   a photodetector;
   a first light-receiving system configured to cause the photodetector to receive first reflected light with a first angle of reflection, the first reflected light generated by reflecting, from a surface, a first light from a light source; and
   a second light-receiving system configured to cause the photodetector to receive second reflected light with a second angle of reflection, different from the first angle of reflection, the second reflected light generated by reflecting, from the surface, a second light from the light source,
   wherein the first light and the second light are generated in a sequential order to generate the first reflected light and the second reflected light in the sequential order,
   wherein a first light-receiving area of the photodetector configured to receive the first reflected light from the surface via the first light-receiving system is spaced apart from a second light-receiving area of the photodetector configured to receive the second reflected light from the surface via the second light-receiving system, and
   wherein the first light-receiving area of the photodetector is spaced apart from an area of the photodetector which reflected light, different from the first reflected light, generated by reflecting the first light from the surface reaches via the second light-receiving system, and the second light-receiving area of the photodetector is spaced apart from an area of the photodetector which reflected light, different from the second reflected light, generated by reflecting the second light from the surface reaches via the first light-receiving system.

2. The optical system according to claim 1, further comprising:
   a first light-projecting system configured to generate the first light and a second light-projecting system configured to generate the second light,
   wherein the first light-receiving system includes a deflector configured to deflect the first reflected light toward the photodetector.

3. The optical system according to claim 2,
   wherein the first reflected light includes regular reflected light of light incident on the surface from the first light-projecting system,
   wherein the second reflected light includes regular reflected light of light incident on the surface from the second light-projecting system.

4. The optical system according to claim 2,
   wherein the first light-receiving system and the second light-receiving system are configured such that a measuring area as a set of positions, on the surface, of light, directed from any points in the first light-receiving area via the first light-receiving system and reaching the surface, is spaced apart from an area as a set of positions, on the surface, of light directed from the any points via the second light-receiving system and reaching the surface.

5. The optical system according to claim 1, further comprising:

a shield configured to shade light directed toward the first light-receiving area from the second light-receiving system.

6. The optical system according to claim 1, further comprising:
   a second photodetector; and
   a third light-receiving system configured to cause the second photodetector to receive third reflected light with a third angle of reflection, different from the first angle of reflection and the second angle of reflection, the third reflected light generated by reflecting, from the surface, a third light from another light source.

7. The optical system according to claim 6, further comprising:
   a third light-projecting system configured to generate the third light,
   wherein the third reflected light includes regular reflected light of light incident on the surface from the third light-projecting system.

8. The optical system according to claim 1, wherein the first angle of reflection or the second angle of reflection is any one of 20°, 45°, 60°, 75° and 85°.

9. An apparatus for measuring optical quality of a surface, the apparatus comprising:
   an optical system comprising:
      a photodetector;
      a first light-receiving system configured to cause the photodetector to receive first reflected light with a first angle of reflection, the first reflected light generated by reflecting, from a surface, a first light from a light source;
      a second light-receiving system configured to cause the photodetector to receive second reflected light with a second angle of reflection, different from the first angle of reflection, the second reflected light generated by reflecting, from the surface, a second light from the light source; and
      a controller connected to the photodetector and the light source, and configured to perform control such that the first light and the second light are generated in a sequential order to generate the first reflected light and the second reflected light in the sequential order and to cause the photodetector to receive the first reflected light and the second reflected light in the sequential order,
      wherein a first light-receiving area of the photodetector configured to receive the first reflected light from the surface via the first light-receiving system is spaced apart from a second light-receiving area of the photodetector configured to receive the second reflected light from the surface via the second light-receiving system, and
      wherein the first light-receiving area of the photodetector is spaced apart from an area of the photodetector which reflected light, different from the first reflected light, generated by reflecting the first light from the surface reaches via the second light-receiving system, and the second light-receiving area of the photodetector is spaced apart from an area of the photodetector which reflected light, different from the second reflected light, generated by reflecting the second light from the surface reaches via the first light-receiving system.

10. The apparatus according to claim 9, wherein the apparatus is configured to measure glossiness as the optical quality.

11. An optical system comprising:
    a first light-projecting system for irradiating first light from a light source to a surface;
    a second light-projecting system, different from the first light-projection system, for irradiating second light from a light source to the surface;
    a first light-receiving system for causing a photodetector to receive first reflected light, wherein the first reflected light is generated by reflecting the first light with a first angle of reflection from the surface, and the first light-receiving system includes a deflector for deflecting the first reflected light toward the photodetector; and
    a second light-receiving system for causing the photodetector to receive second reflected light, wherein the second reflected light is generated by reflecting the second light with a second angle of reflection, different from the first angle of reflection, from the surface;
    wherein a first light-receiving area of the photodetector arranged to receive the first reflected light from the surface via the first light-receiving system is spaced apart from a second light-receiving area of the photodetector arranged to receive the second reflected light from the surface via the second light-receiving system, characterized in that
    the first light-receiving area of the photodetector is spaced apart from an area of the photodetector which reflected light, different from the first reflected light, generated by reflecting the first light from the surface reaches via the second light-receiving system, and the second light-receiving area of the photodetector is spaced apart from an area of the photodetector which reflected light, different from the second reflected light, generated by reflecting the second light from the surface reaches via the first light-receiving system.

12. The optical system according to claim 11, further comprising:
    a first light source as the light source from which the first light-projecting system irradiates the first light; and
    a second light source, different from the first light source, as the light source from which the second light-projecting system irradiates the second light.

13. The optical system according to claim 11,
    wherein the first reflected light includes specular reflected light of light incident on the surface from the first light-projecting system,
    wherein the second reflected light includes specular reflected light of light incident on the surface from the second light-projecting system.

14. The optical system according to claim 11, further comprising:
    a shield for shading light directed toward the first light-receiving area from the second light-receiving system.

15. The optical system according to claim 11, further comprising:
    a third light-receiving system for causing a second photodetector to receive third reflected light with a third angle of reflection, different from the first angle of reflection and the second angle of reflection, from the surface.

16. The optical system according to claim 15, further comprising:
    a third light-projecting system for irradiating third light from a light source of the surface,
    wherein the third reflected light is generated by reflecting the third light from the surface, wherein the third reflected light includes specular reflected light of light incident on the surface from the third light-projecting system.

17. The optical system according to claim 11, wherein the first angle of reflection or the second angle of reflection is any one of 20°, 45°, 60°, 75° and 85°.

18. The optical system according to claim 11, wherein the first light-receiving area corresponds to an aperture angle of the first light-receiving system defined by a standard, and the second light-receiving area corresponds to an aperture angle of the second light-receiving system defined by the standard.

19. An apparatus for measuring optical quality of a surface, the apparatus comprising:
an optical system as defined in claim 11.

20. The apparatus according to claim 19, wherein the apparatus is configured to measure glossiness as the optical quality.

* * * * *